(12) United States Patent
Berry

(10) Patent No.: US 8,972,882 B2
(45) Date of Patent: Mar. 3, 2015

(54) USER INTERFACES AND SYSTEMS FOR ORAL HYGIENE

(71) Applicant: Orca Health, Inc., Sandy, UT (US)

(72) Inventor: Matthew M. Berry, Highland, UT (US)

(73) Assignee: Orca Health, Inc., Sandy, UT (US)

( * ) Notice: Subject to any disclaimer, the term of this patent is extended or adjusted under 35 U.S.C. 154(b) by 201 days.

(21) Appl. No.: 13/754,250

(22) Filed: Jan. 30, 2013

(65) Prior Publication Data

US 2014/0215370 A1    Jul. 31, 2014

(51) Int. Cl.
*G06F 3/0486* (2013.01)
*G06F 3/0484* (2013.01)
*G06Q 50/22* (2012.01)

(52) U.S. Cl.
CPC ............ *G06F 3/04845* (2013.01); *G06Q 50/22* (2013.01)
USPC ............ 715/769; 715/764; 434/262; 434/263

(58) Field of Classification Search
CPC ..................................................... G06F 3/0486
USPC ......................................................... 715/769
See application file for complete search history.

(56) References Cited

U.S. PATENT DOCUMENTS

| | | | |
|---|---|---|---|
| 2,780,002 A * | 2/1957 | Shea et al. ..................... 434/263 |
| 4,221,060 A * | 9/1980 | Moskowitz et al. .......... 434/264 |
| 4,812,127 A * | 3/1989 | Hernandez ..................... 434/264 |
| 5,085,236 A * | 2/1992 | Odneal et al. ................. 132/325 |
| 5,120,229 A * | 6/1992 | Moore et al. .................. 434/263 |
| 5,232,370 A * | 8/1993 | Hoye .............................. 434/263 |
| 5,688,118 A * | 11/1997 | Hayka et al. .................... 433/27 |
| 5,730,654 A * | 3/1998 | Brown ................................ 463/1 |
| 5,748,907 A | 5/1998 | Crane |
| 5,766,016 A | 6/1998 | Sinclair et al. |
| 5,924,074 A | 7/1999 | Evans |
| 5,944,531 A * | 8/1999 | Foley et al. ..................... 434/263 |
| 6,152,731 A * | 11/2000 | Jordan et al. ..................... 433/69 |
| 6,227,850 B1 * | 5/2001 | Chishti et al. .................... 433/24 |
| 6,383,135 B1 | 5/2002 | Chikovani et al. |
| 7,001,270 B2 * | 2/2006 | Taub ................................... 463/1 |
| 7,107,547 B2 | 9/2006 | Cule et al. |
| 7,180,524 B1 * | 2/2007 | Axelrod ......................... 345/593 |
| 7,962,348 B2 | 6/2011 | Dew et al. |
| 7,976,388 B2 * | 7/2011 | Park et al. ........................ 463/37 |
| 8,016,678 B1 * | 9/2011 | Hutter et al. ..................... 463/42 |
| 8,062,089 B2 * | 11/2011 | Hardin et al. .................. 446/175 |
| 8,662,900 B2 * | 3/2014 | Bell et al. ........................ 434/263 |
| 8,702,238 B2 * | 4/2014 | Berry et al. ..................... 351/223 |
| 8,843,852 B2 * | 9/2014 | Berry et al. ..................... 715/823 |
| 2002/0082865 A1 | 6/2002 | Bianco et al. |
| 2003/0208324 A1 | 11/2003 | Bellwood et al. |
| 2004/0002873 A1 * | 1/2004 | Sachdeva ........................... 705/2 |
| 2005/0104896 A1 | 5/2005 | Kerr |

(Continued)

OTHER PUBLICATIONS

Screenshot of brushing and flossing treatment manufactured by Scantlebury Orthodontics, Wayback Machine, available at <http://web.archive.org>, archived on Apr. 29, 2012, 23 pages.*

(Continued)

*Primary Examiner* — Reza Nabi
(74) *Attorney, Agent, or Firm* — Workman Nydegger

(57) ABSTRACT

Computer interfaces are provided for exploring dental anatomy, for accessing information related to dental conditions, for learning oral hygiene and for cataloguing events. Some of the learning interfaces provide interactive elements for practicing the flossing and brushing of teeth.

18 Claims, 13 Drawing Sheets

(56) References Cited

U.S. PATENT DOCUMENTS

| | | | |
|---|---|---|---|
| 2005/0279378 A1* | 12/2005 | Lorch | 132/321 |
| 2006/0040246 A1* | 2/2006 | Ding et al. | 434/263 |
| 2006/0190301 A1* | 8/2006 | Sachdeva | 705/3 |
| 2007/0236514 A1* | 10/2007 | Agusanto et al. | 345/646 |
| 2007/0242069 A1 | 10/2007 | Matsue | |
| 2007/0270221 A1* | 11/2007 | Park et al. | 463/37 |
| 2008/0027917 A1 | 1/2008 | Mukherjee | |
| 2008/0136838 A1 | 6/2008 | Goede et al. | |
| 2008/0177602 A1 | 7/2008 | Sopher et al. | |
| 2008/0242953 A1 | 10/2008 | Dew et al. | |
| 2010/0015589 A1* | 1/2010 | Lehavi | 434/263 |
| 2010/0070297 A1 | 3/2010 | Kharraz Tavakol et al. | |
| 2010/0070300 A1 | 3/2010 | Anderson et al. | |
| 2010/0257214 A1 | 10/2010 | Bessette | |
| 2010/0287001 A1 | 11/2010 | Pearce et al. | |
| 2010/0311028 A1* | 12/2010 | Bell et al. | 434/263 |
| 2011/0145693 A1 | 6/2011 | Mutic | |
| 2011/0170752 A1 | 7/2011 | Martin et al. | |
| 2011/0264503 A1 | 10/2011 | Lenahan et al. | |
| 2012/0159391 A1* | 6/2012 | Berry et al. | 715/823 |
| 2012/0206694 A1 | 8/2012 | Raskar | |
| 2012/0280988 A1* | 11/2012 | Lampotang et al. | 345/419 |
| 2013/0071827 A1* | 3/2013 | Berry et al. | 434/267 |
| 2013/0141697 A1* | 6/2013 | Berry et al. | 351/223 |
| 2013/0142367 A1* | 6/2013 | Berry et al. | 381/315 |
| 2013/0211284 A1 | 8/2013 | Berry et al. | |
| 2013/0315452 A1* | 11/2013 | Berry et al. | 382/128 |
| 2014/0022283 A1* | 1/2014 | Chan et al. | 345/633 |
| 2014/0122096 A1* | 5/2014 | Berry et al. | 705/2 |
| 2014/0154655 A1* | 6/2014 | Bell et al. | 434/262 |
| 2014/0168606 A1* | 6/2014 | Berry et al. | 351/223 |
| 2014/0173508 A1* | 6/2014 | Berry et al. | 715/794 |
| 2014/0204118 A1* | 7/2014 | Berry et al. | 345/633 |

OTHER PUBLICATIONS

U.S. Appl. No. 14/477,540, filed Sep. 4, 2014, Berry et al.
U.S. Appl. No. 14/251,400, filed Apr. 11, 2014, Mainwaring et al.
U.S. Appl. No. 62/045,968, filed Sep. 4, 2014, Mainwaring et al.
VueCare Media, Vue Simulator, Demo video accessed at: http://www.vuecaremedia.com/vuesim_demo.html, copyright 2010. (The month of Publication is irrelevant since the year of Publication is clearly prior to the filing of the Application).
VueCare Media, Vue Simulator, About page accessed at: http://web.archive.org/seb/20110207031345/http://vuecaremedia.com/vuesim.html, available at least as early as Feb. 7, 2011.
VueCare Media: The Eye Channel Network press release accessed at: http://vuecaremedia.com/Final%20Press%20Release%2011-1-10.pdf, Created Dec. 23, 2010.
Biggs, John, Up Close With Biodigital's 3D Human Simulator [TCTV]TCTechCrunch, Apr. 25, 2012, http://techcrunch.com/2012/04/25/up-close-with-biodigitals-3d-human-simulator-tctv/.
Pivi & Co, FatBooth, http://itues.apple.com/us/app/fatbooth/id372268904?mt=8, Available at least as early as Dec. 19, 2012, Version 3.4.
Welcome to the AR Lungs Website, http://www.arlungs.com/, Available at least as early as Jan. 7, 2013.
Mirracle, http://mirracle.de/, First Prototype of Magic Mirror, Jan. 3, 2011.
U.S. Appl. No. 13/093,272, filed Dec. 4, 2013, Office Action.
U.S. Appl. No. 13/093,272, filed May 16, 2014, Notice of Allowance.
U.S. Appl. No. 13/237,530, filed Feb. 1, 2013, Preinterview First Office Action.
U.S. Appl. No. 13/237,530, filed Apr. 19, 2013, Office Action.
U.S. Appl. No. 13/237,530, filed Oct. 1, 2013, Office Action.
U.S. Appl. No. 13/237,530, filed Mar. 20, 2014, Office Action.
U.S. Appl. No. 13/838,865, filed Nov. 18, 2013, Office Action.
U.S. Appl. No. 13/838,865, filed May 15, 2014, Office Action.
U.S. Appl. No. 13/477,794, filed May 20, 2014, Office Action.
U.S. Appl. No. 13/477,794, filed Aug. 29, 2014, Notice of Allowance.
U.S. Appl. No. 13/663,820, filed Jun. 6, 2014, Office Action.
U.S. Appl. No. 13/663,820, filed Oct. 2, 2014, Office Action.
U.S. Appl. No. 13/747,595, filed Oct. 8, 2014, Office Action.

* cited by examiner

USER INTERFACES AND SYSTEMS FOR ORAL HYGIENE

CROSS-REFERENCE TO RELATED APPLICATIONS

Not applicable.

BACKGROUND

1. The Field of the Invention

The present invention is generally directed to computer interfaces and, even more particularly, to the presentation and use of computer interfaces for promoting learning and healthy behaviors related to oral hygiene.

2. The Relevant Technology

The use of computer interfaces in the medical community is well-known. For instance, it is common for medical professionals to utilize computer interfaces to access patient records and to research medical topics.

Some computer interfaces include interactive elements in the form of text or graphical objects that are configured as links which, when selected, access and display multimedia content and other information.

While many types of computer interfaces have been developed over the years, there is a persistent need for additional interfaces that are capable of promoting learning and healthy behaviors.

BRIEF SUMMARY OF THE INVENTION

The present invention extends to methods, systems, and computer program products for presenting and using computer interfaces that are capable of promoting learning and behaviors related to oral hygiene.

In some embodiments, computing interfaces are provided to facilitate interactive learning about dental anatomy and conditions associated with the dental anatomy. Some interfaces also include interactive tools for teaching behaviors related to oral hygiene, including interactive brushing and flossing activities.

Some interfaces are configured for cataloguing user behaviors and events related to oral hygiene and, in some instances, for communicating this information to appropriate medical professionals.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

User interfaces of the invention can be utilized to promote learning and healthy behaviors related to oral hygiene like eating properly, good habits, brushing teeth and flossing.

Users can interact with interfaces of the invention to learn about the anatomy and conditions associated with their teeth. Some interfaces provide interactive brushing and flossing tools and mechanisms for logging events related to oral hygiene and, in some instances, mechanisms for communicating related information to medical professionals.

The terms 'computing system,' 'system,' 'computing device,' and 'device,' which are used interchangeably herein, all refer to computing systems that include physical computing hardware, such as a physical computing processor, a display screen, a storage device (e.g., computer memory and/or disk storage), and/or other computer hardware as described in more detail with reference to FIG. 12.

In many embodiments, the computing systems are mobile devices (e.g., phones, tablets, notebook computers, portable gaming device, etc.) that are utilized to interact with the user interfaces of the invention. In other embodiments, the computing systems comprise stationary devices (e.g., desktop computers, gaming consoles, televisions, servers, kiosks, etc.) or a combination of stationary and mobile devices.

Preferably, although not necessarily, the computing systems have multi-touch screens that are operable to receive and process touch input and to display relevant output, although other input and output devices can also be used. Accordingly, the term 'user-input', as referenced herein, can include touch input directed at a display object that is rendered on a display screen. The touch input can be a single point and single tap touch, a multi-point touch, a touch and drag input, a multi-tap touch and/or any other combination of touch input.

Oral Hygiene Interfaces

Figure 1:
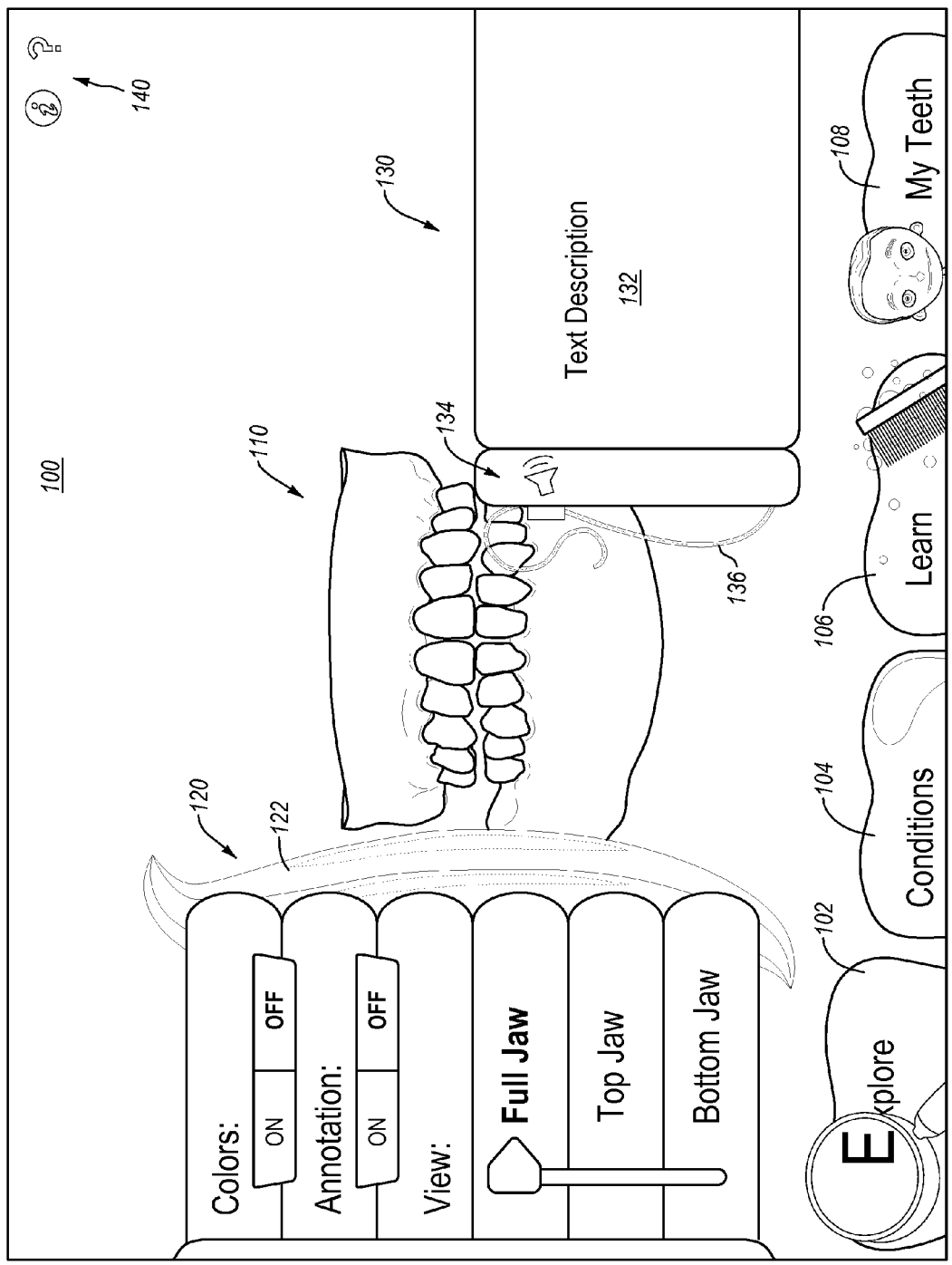
FIG. 1 illustrates a user interface displaying dental anatomy, a plurality of display controls, interactive links, and an information frame.

FIG. 1 illustrates one example of a user interface, according to the invention, for displaying dental anatomy. As shown, this interface 100 includes a plurality of interactive links (102, 104, 106, 108) which are operable, when selected by touch input or other input, to access a specific interface display related to the selected link. In the present embodiment, link 102 has been selected for providing a display that is operable to explore dental anatomy. The display of dental anatomy 110 in the present embodiment is controlled by the setting of a plurality of display controls 120.

The display controls 120 are accessible through a control handle 122 that is displayed to the user. The control handle 122 is operable to selectably hide or expose the plurality of display controls 120 when the control handle 122 is selected.

The display controls 120 include selectable controls that are operable for setting the color, annotation and view properties of the dental anatomy 110. In the present embodiment, the dental anatomy 110 is displaying a full jaw with no annotations or coloring, based on the settings of the display controls 120.

The displayed dental anatomy 110 is an interactive display object that can be selected and rotated/moved in response to user input directed at the dental anatomy 110.

In some embodiments, an information frame 130 is also provided to display textual descriptions 132 related to the dental anatomy 110 and/or audio links 134 that are operable (when selected) to initiate the playing of audio descriptions related to the dental anatomy 110. These descriptions can be generic descriptions or customized descriptions related to a particular user's medical records.

The information frame 130 can be selectably exposed and/or hidden in response to user input directed at a handle 136 to the information frame 130.

Other links 140 provide selectable access to other menu interfaces for controlling settings associated with the display controls, information frame and the displayed anatomy, as well as for accessing additional information related to the interface and for accessing information related to medical professionals and other specialists familiar with the displayed anatomical objects.

Figure 2:
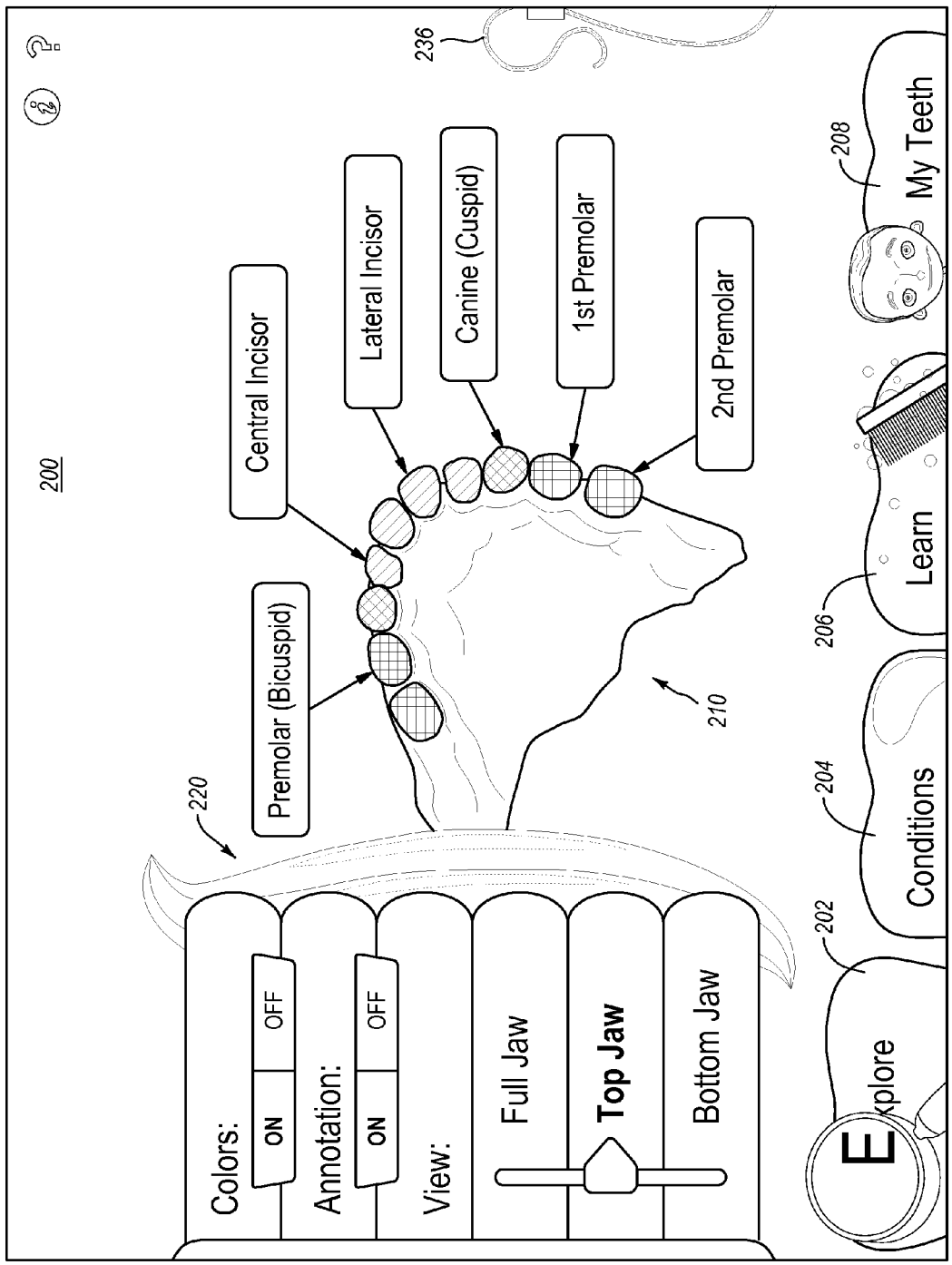
FIG. 2 illustrates an embodiment similar to the interface of FIG. 1, with similar interactive links, but wherein the display controls have a different selected configuration for a different display of dental anatomy, and wherein the information frame is hidden.

FIG. 2 illustrates another interface 200 similar to the interface 100 of FIG. 1, with similar interactive links (202, 204, 206, 208) and display controls 220. However, in this embodiment, the dental anatomy 210 is rendered with only a display of the top jaw, with coloring added to the teeth (reflected by shading), and annotations turned on. This display corresponds directly to the settings of the display controls 220, which have been adjusted from the settings in FIG. 1, with coloring turned on, annotations turned on and the view set to display the top jaw only.

With specific regard to the coloring, it will be appreciated that the types and variations of coloring setting can cause different teeth to be rendered with different colors or simply different shades of a same color. The coloring setting can also apply different colors to different individual teeth or different groupings of teeth. Color settings can also be used to color different portions of a single tooth with different colors to highlight specific features or anatomy. Coloring can also be used to highlight other dental anatomy, besides the teeth. For instance, by way of example, coloring can be used to distinguish the gums from other tissue.

In some embodiments, the coloring is used to distinguish different types of teeth. For instance, the premolars, canines and incisors can each be displayed with different coloring, as shown by the different shading. However, the coloring variations can also include using different primary colors or other color pallets for each of the different types of teeth.

When the dental anatomy is showing a user's own mouth (based on dental records or other medical records), the coloring can be used to identify and highlight specific trouble areas (e.g., cavities, infected teeth, broken teeth, abscessed teeth, and so forth).

Different annotations can also be used to identify and distinguish specific features, anatomy, conditions or other related information. In some embodiments, the annotations are linked to medical records specific to a particular user. In other embodiments, the annotations are fixed labels.

As also shown in FIG. 2, the handle 236 is against the boarder of the interface, such that the information frame is hidden. When the handle 236 is selected with user input, an information frame, similar to the information frame 130 of FIG. 1 is rendered.

Figure 3:
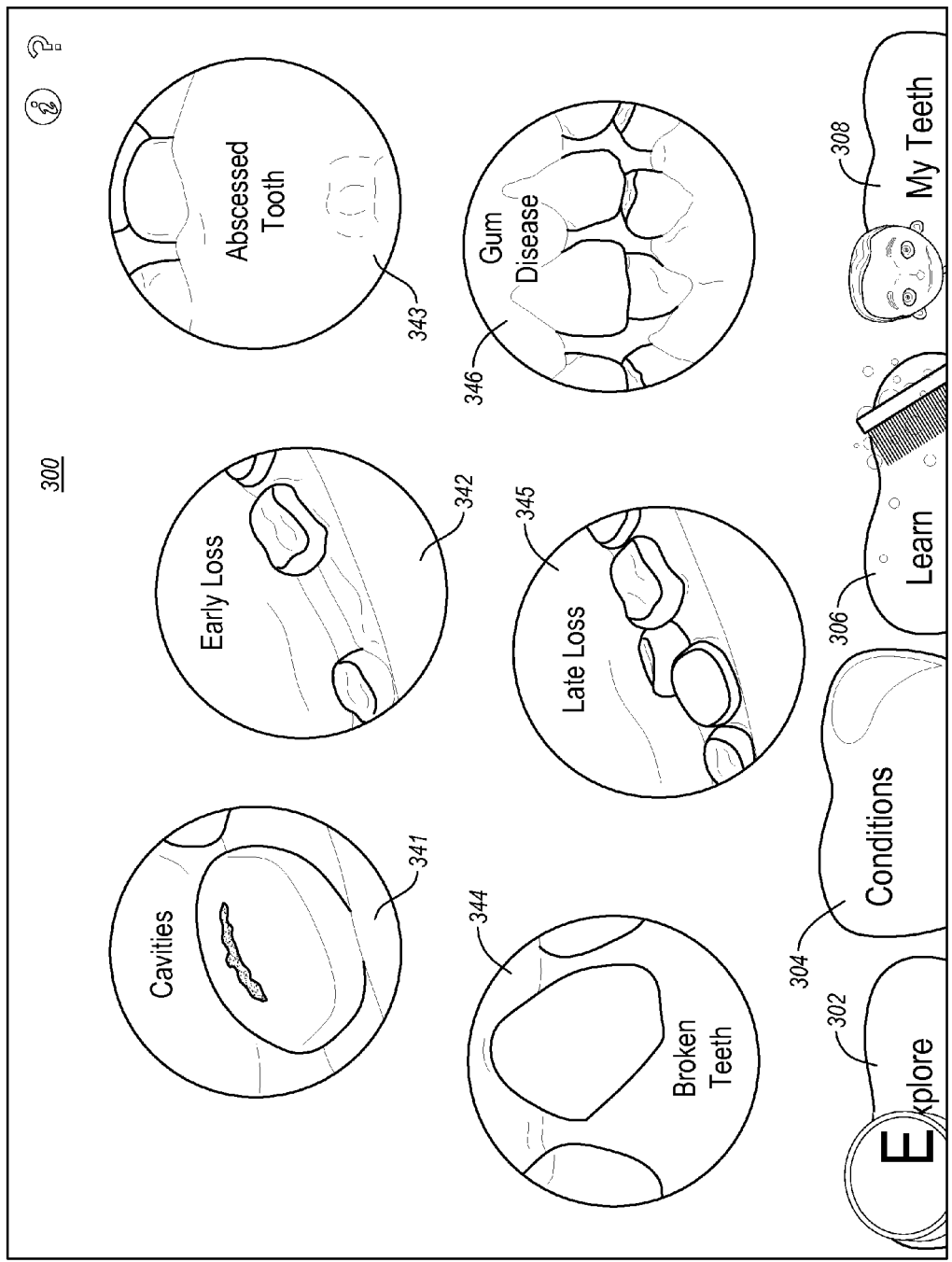
FIG. 3 illustrates an embodiment of an interface displaying a plurality of interactive links corresponding to a plurality of different dental conditions.

FIG. 3 illustrates an embodiment in which a plurality of interactive links related to medical conditions (341, 342, 343, 344, 345 and 346). Selection of any of these links will initiate the display of additional information related to the condition associated with the selected link. For instance, selection of link 341 will initiate the rendering of a display related to the causes and/or treatments of a cavity. Similarly, selection of link 342 will initiate the rendering of a display related to the causes and/or treatments of early tooth loss, selection of link 343 will initiate the rendering of a display related to the causes and/or treatments of an abscessed tooth, selection of link 344 will initiate the rendering of a display related to the causes and/or treatments of broken teeth, selection of link 345 will initiate the rendering of a display related to the causes and/or treatments of late tooth loss, and selection of link 346 will initiate the rendering of a display related to the causes and/or treatments of gum disease.

Each of the displays presented in response to the selection of one of the links (341, 342, 343, 344, 345 and 346) includes one or more of textual information, audio information, static images and/or video related to the corresponding conditions.

The displays also include additional information or links to additional information that identify medical professionals and other specialists familiar with the displayed conditions. The information identifying the medical professionals can be provided from a medical professional subscribed for an advertising service and/or can be extracted from third party medical databases.

The interface 300 shown in FIG. 3 is accessible through the selection of link 304. Other links 302, 306 and 308 can be used to access other display interfaces, as described herein.

Figure 4:
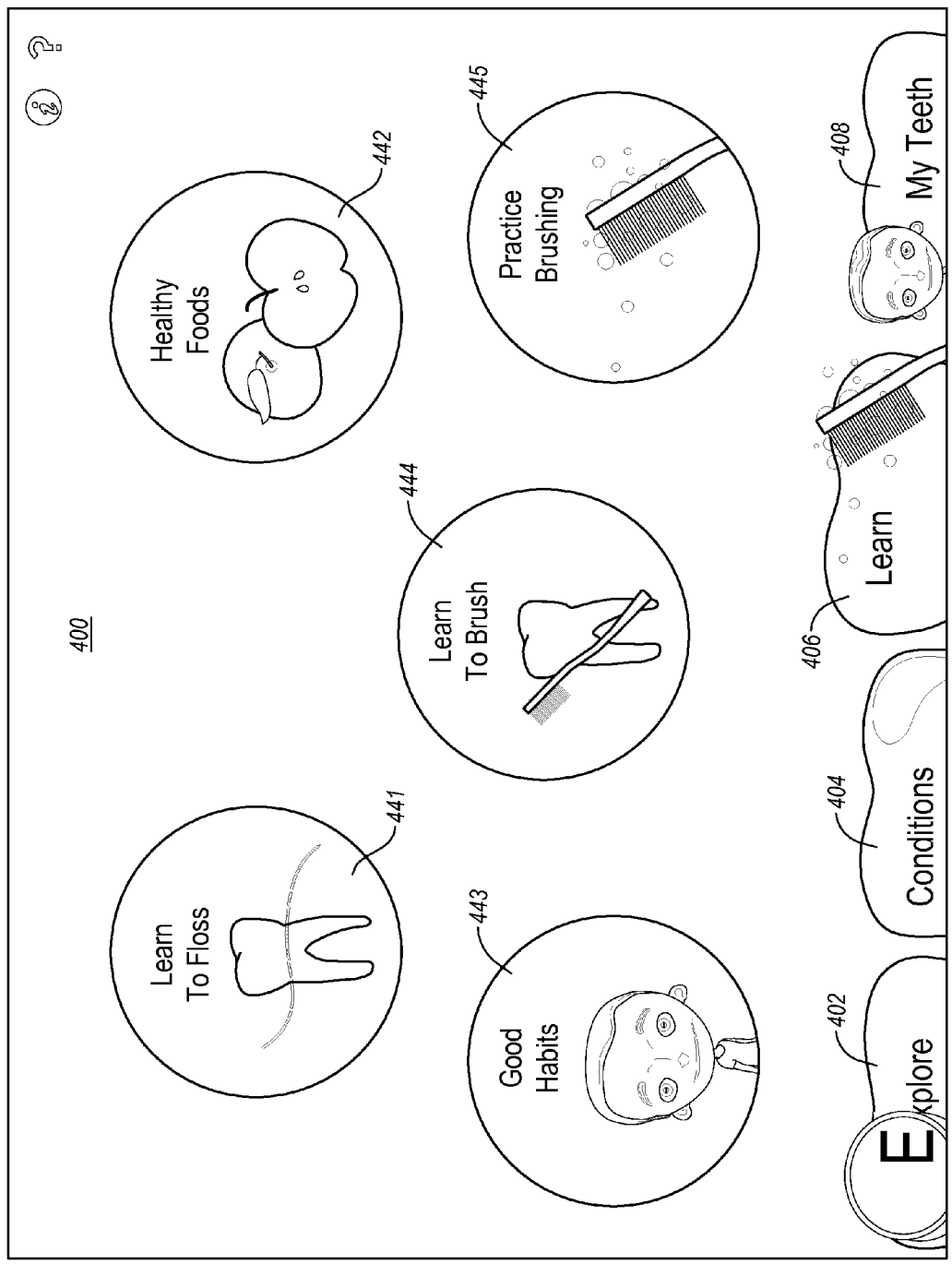
FIG. 4 illustrates an embodiment of an interface that is displaying a plurality of interactive links to a plurality of nested learning and behavior interfaces.

When link 306 is selected, a user is presented with an interface 400 that displays links to different learning interfaces for learning more about oral hygiene, as shown and described in reference to FIG. 4.

The interface 400 of FIG. 4 includes various links 402, 404, 406 and 408, as described above, as well as links to other interfaces associated with learning to floss 441, healthy foods, 442, good habits 443, learning to brush 444 and practicing brushing 445. Various other types of links can also be provided, if desired, to other categories or subcategories related to oral hygiene.

The healthy foods link 442, when selected, initiates the rendering of multimedia content related to healthy foods. The selection of the good habits link 443, initiates the rendering of multimedia content related to good habits for promoting oral hygiene. The selection of the learn to floss and learn to brush links (441 and 444) provide selectable access to interface displays that present multimedia content related to flossing and brushing, respectively.

The multimedia content can include any combination of text, images, video and/or audio that is used to provide information related to the selected link(s). In some embodiments, the multimedia content can also include interactive elements and/or haptic feedback.

In some embodiments, the 'learn to floss' and 'learn to brush' links (441 and 444) operate similar to the 'practice brushing' link 445, which is operable (when selected) to render an interactive display for practicing flossing and brushing, as described in more detail below with reference to FIGS. 5-8.

Figure 5:
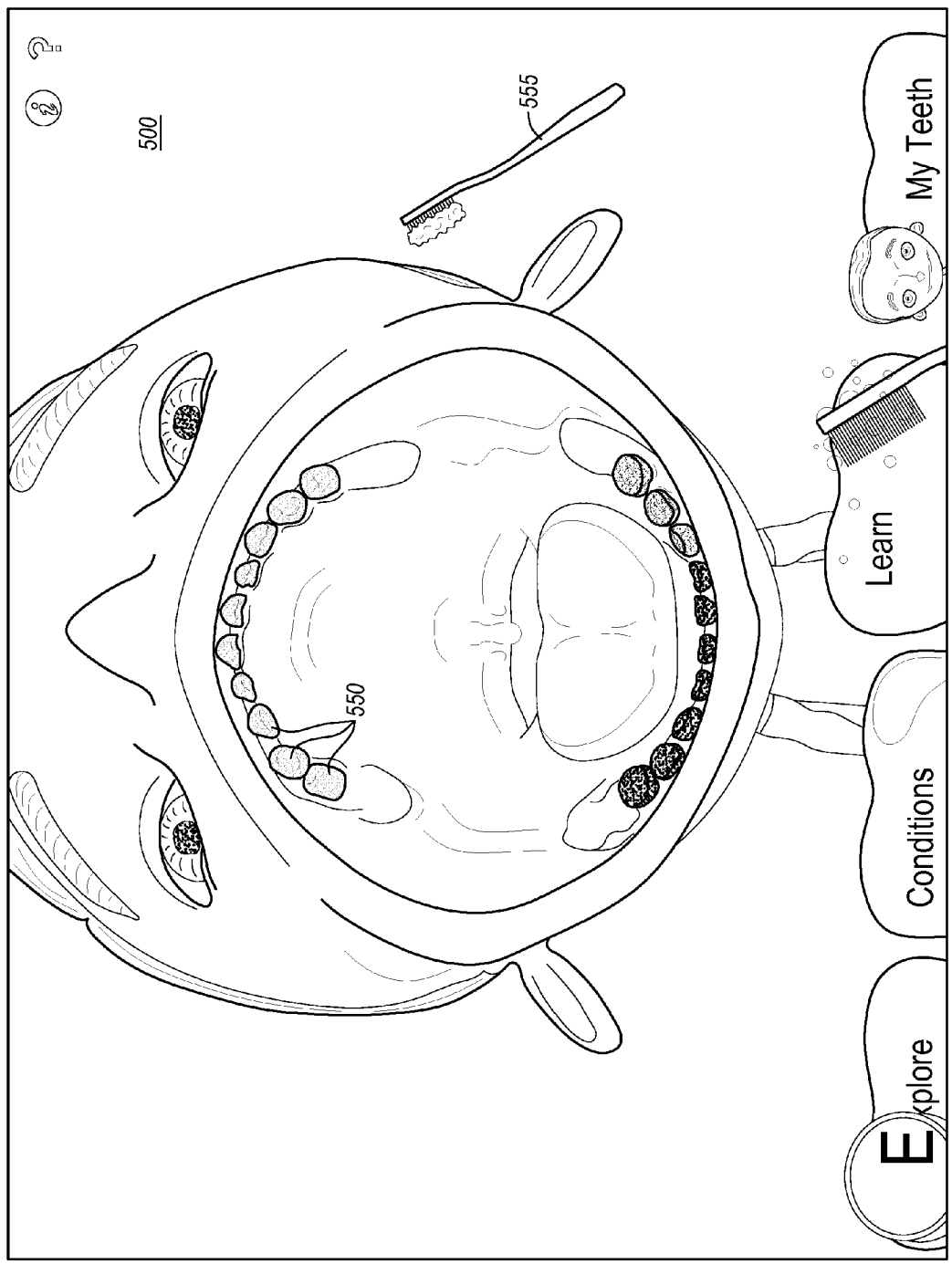
FIG. 5 illustrates an embodiment of an interface tool that can be used to learn about and practice brushing teeth, wherein the interface is displaying an illustration of teeth and an interactive toothbrush that can be moved relative to the teeth to simulate brushing of the teeth.

FIG. 5 illustrates an embodiment of an interface 500 that is displayed in response to selection of the 'learn to brush' or 'practice brushing' links (444, 445). This interface operates as a tool that can be used to learn about and practice brushing teeth. As shown, an image of a mouth is presented with a plurality of teeth 550. These teeth 550 are displayed in a first state of relative uncleanliness. An interactive toothbrush 555 is also displayed, which is operable to be moved about the display screen in response to user input directed at the interactive toothbrush 550. For instance, a user can place their finger on the interactive toothbrush 550 and drag their finger across the screen and the interactive toothbrush 550 will move with their finger.

In some embodiments, the interactive toothbrush 550 can also be rotated in response to multiple touch inputs on the toothbrush 555 that are moved in different directions.

When the head of the toothbrush 555 comes in contact with the displayed teeth the interface will generate a sound of brushing. Similarly, the movement of the brush head over the teeth is operable to change the displayed state of the teeth from a relative state of uncleanliness to a relative state of cleanliness. The amount of time that is required to brush any particular tooth, prior to the display of that tooth changing to a state of cleanliness can vary, as desired, to accommodate any need or preference. For instance, a tooth may transition to a displayed state of cleanliness after only a few seconds (e.g., 1, 2, 3, 4, or 5 seconds) or many seconds (6, 7, 8, 9, 10 or more seconds) of detected brushing at the tooth being brushed.

The change in display state can include changing a shading and or coloring of the entire tooth or a portion of the tooth. For instance, changing the display state can include brightening or lightening the coloring of the displayed teeth In some embodiments, the brushing of the teeth will only cause the teeth to change to a displayed state of cleanliness when the brushing is performed with a certain frequency, as controlled by settings associated with the interface.

In some embodiments, the detected brushing movement is also identified and distinguished to determine whether the brushing is a back and forth motion in a horizontal, vertical or other alignment, or whether the brushing is performed in a circular motion. Different settings can be used to require a certain amount of lateral or circular brushing prior to changing the displayed state of the teeth. Each tooth can also be assigned specific requirements for the amount of time and type of brushing that must be detected prior to changing the displayed state of the tooth to a state of cleanliness.

The transition of the teeth, from a displayed state of relative uncleanliness to a state of cleanliness can be performed gradually and dynamically responsive to the brushing that is taking place, or instantaneously and abruptly once a sufficient amount of time and/or type of brushing has been detected.

The transition of the teeth from a displayed state of relative uncleanliness to a state of cleanliness can also be performed on a single tooth or a plurality of adjacent teeth most proximate the head of the toothbrush 555 during the detected brushing.

Figure 6:
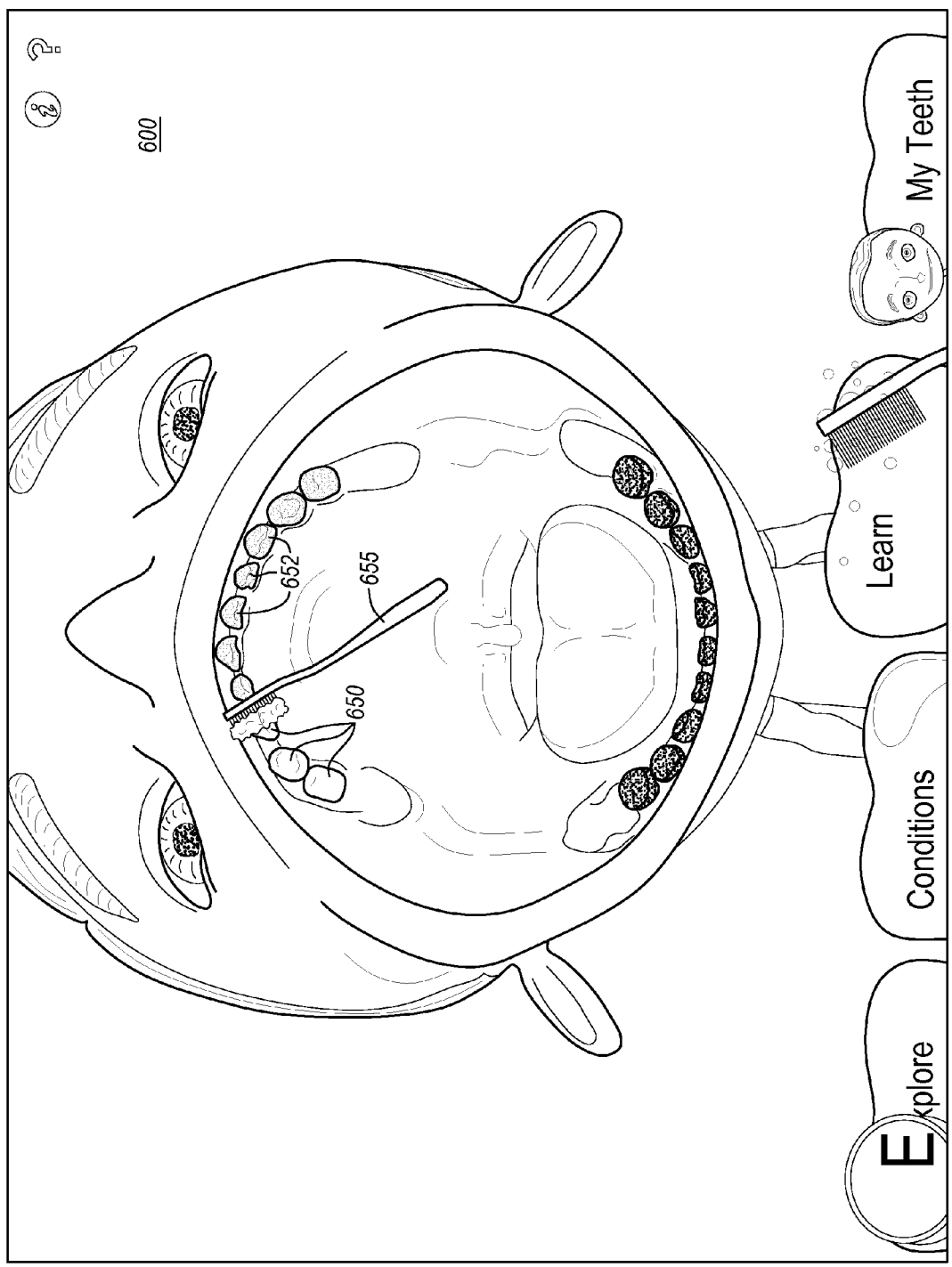
FIG. 6 illustrates an embodiment of an interface similar to the interface of FIG. 5, wherein the interactive toothbrush has been moved over some of the teeth.

FIG. 6 illustrates an interface 600 in which some of the teeth 650 have been brushed to a state or relative cleanliness and in which some of the teeth 652 (shown in a relative state of uncleanliness) still need to be brushed.

During use, a user can move the toothbrush 655, in a brushing motion over all of the teeth until all of the teeth are changed to a relative state of cleanliness. This interface tool can be particularly useful for helping to instruct children and other users how to properly brush their teeth and to develop habits for brushing teeth.

Figure 7:
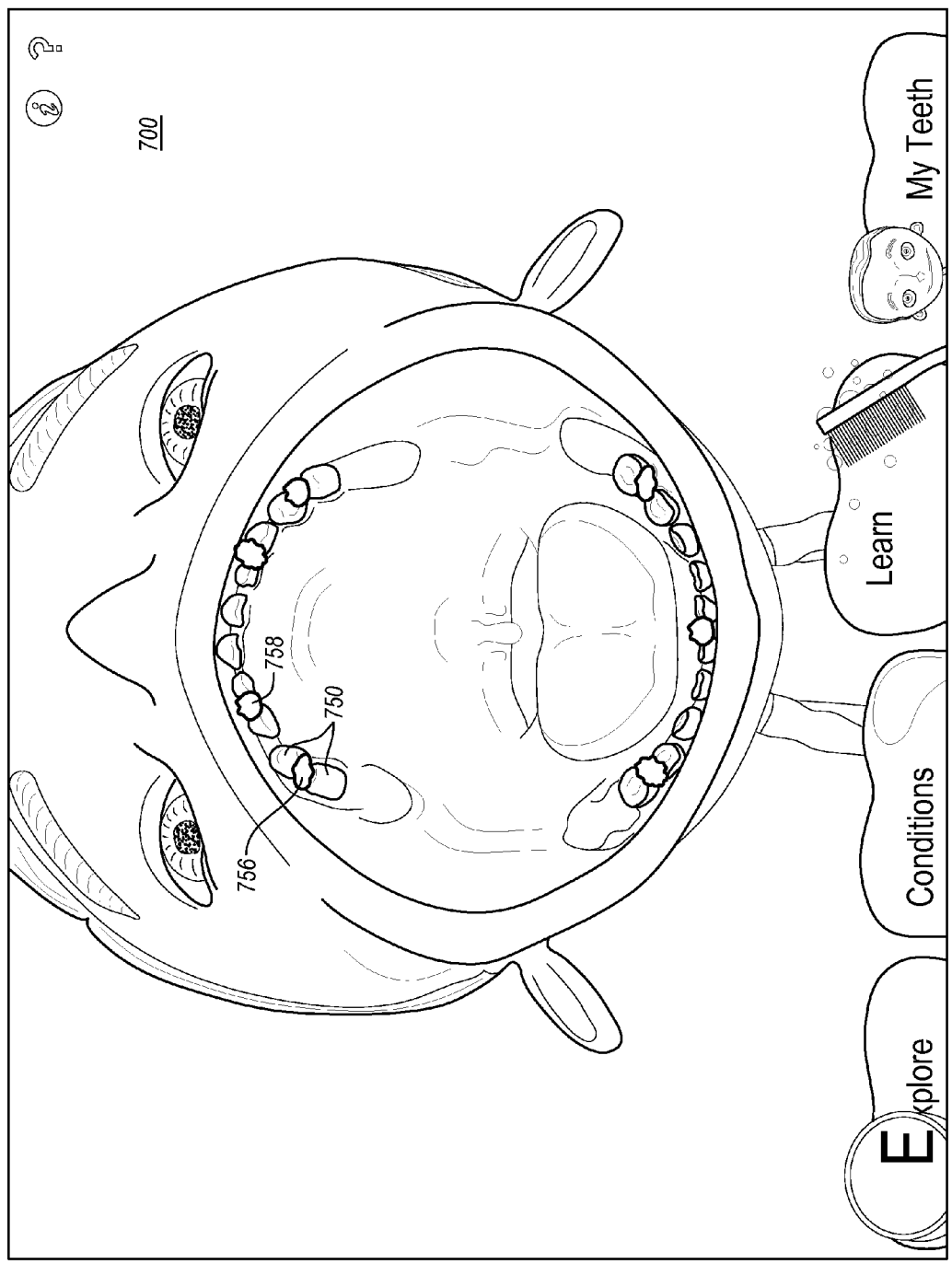
FIG. 7 illustrates an embodiment of an interface that can be used to learn about and practice flossing teeth, wherein the interface is displaying an illustration of teeth with food particles disposed between some of the teeth.

FIG. 7 illustrates an embodiment of an interface 700 that can be accessed through link 441 or another link and which is useable to learn about flossing and to practice flossing teeth. As shown, a mouth is displayed with teeth 750 in a first state of relative uncleanliness (with food particles 756, 758 stuck between the teeth).

Figure 8:
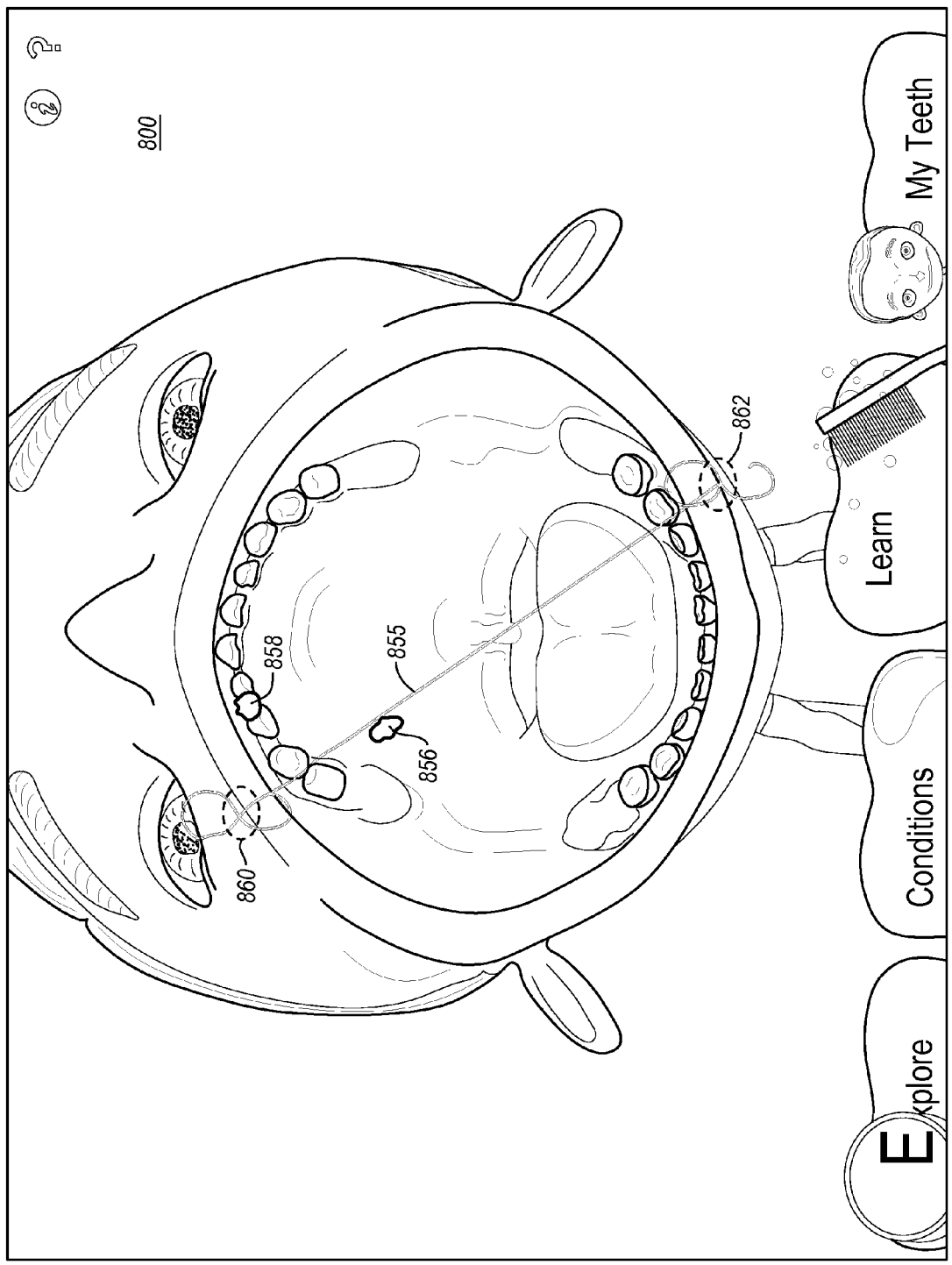
FIG. 8 illustrates an embodiment of an interface similar to the interface of FIG. 7, wherein interactive floss is positioned between the teeth.

When a user touches different portions of the display screen, an interactive floss object is displayed between the two touch points. For instance, as shown in FIG. 8, the interface 800 shows interactive floss 855 that is disposed between two touch points (860 and 862) where the user's fingers are touching the display. The user's fingers are not presently illustrated in this figure to add clarity to the other illustrated elements.

When the user moves their fingers in a back and forth motion, cooperatively, the interactive floss is moved with the finger movements. In this manner, the user can practice the coordinated movement that is required to floss between teeth.

When the user moves the floss between the teeth, the food particles are removed, such as particle 856, which has been removed from between the teeth in response to current flossing activity. Food particle 858 will also be removed once sufficient flossing is performed between the teeth where the food particle 858 is currently located. When the food particles are removed from the teeth, the teeth are effectively changed to a new display state (one of relative cleanliness).

The amount of flossing required for removing the food particles from between the teeth can be set to any preferred duration. Similarly, the type of flossing motion that is required can also be set, so as to require a particular traversal and/or distance of the floss through the teeth, a type of flossing motion or quantity of flossing motions, and so forth.

Although not shown, the floss can bend around particular teeth when the point of contact with the particular teeth does not remain perfectly aligned between the user's fingers. Alternatively, movement of the user's fingers can simply move the floss to other teeth when the particular teeth are no longer aligned between the user's fingers.

In some embodiments, the movement of the user's fingers must be coordinated, in order to perform the flossing. Accordingly, embodiments of the invention include detecting and requiring the distance between touch points 860 and 862 to remain relatively the same (within a certain threshold of variability, such as within a few millimeters, centimeters, and so forth), even as the particular locations of the touch points 860, 862 is changed, in order to move the floss and/or to remove the food particles.

While the interfaces described with reference to FIGS. 5-8 have been shown with animated dental anatomy, it will be appreciated that these interfaces can also be used by displaying a user's actual mouth and by using augmented reality to modify the display of the user's teeth during the brushing and flossing activities. Images of the user's mouth can be obtained from medical records or can be uploaded by the user.

Figure 9:
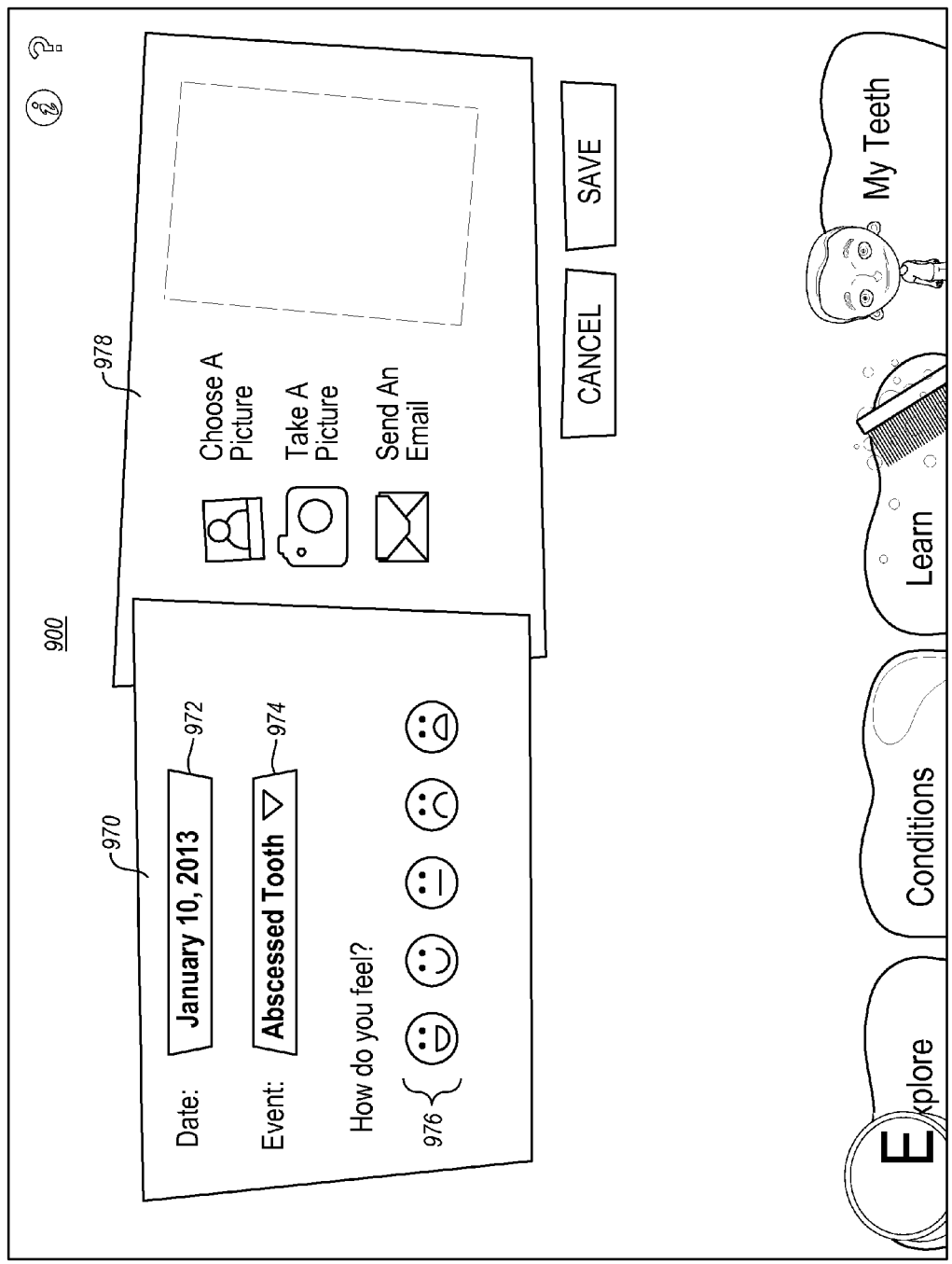
FIG. 9 illustrates an interface that can be used to log events.

Attention is now directed to FIG. 9 which includes a display of an interface 900 for logging events. As shown, this interface includes a first frame 970 that includes a date field 972 for identifying a date of an event and a type field 974 for identifying a type of event. These fields can be populated by selecting an entry from pull-down menus and/or by receiving user input in the form of typed character input provided through the fields 972, 974.

A perception scale 976 is also provided for receiving user input selecting one or more of the selectable objects in the perception scale 976 that reflect how a user feels. This can be used to track relative changes with regard to a particular event and the date when the feelings are logged. The perception scale 976 includes a plurality of plurality of selectable icons (emoticons) associated with perceived feelings related to the event and event data.

The interface 900 also provides a frame 978 with options for browsing and selecting images from a database related to the event, for taking new pictures and for sending emails. When a user selects the option to choose a picture, the user is presented a browsing interface or a file index for identifying and selecting an image to associate with the event. When a user selects the 'take a picture' option, the user's computing device turns on a camera mode with options for taking a picture that will be manually or automatically linked to the event. The email option, when selected, initiates the creation of an email for sending the event data logged with the interface 900 to a medical professional.

In some embodiments, the selection of the email option automatically populates email fields with appropriate contact information, subject headers and body information that corresponds to the event data entered with the interface 900 and/or that is identified as being associated with the event and/or medical professionals that are determined to be knowledgeable about the logged event or corresponding events.

In some embodiments, the events are catalogued with the user's own device. In other embodiments, the events are catalogued by a medical professional and transmitted to the user device, for corresponding cataloguing at the user's device or related storage system.

Figure 10:
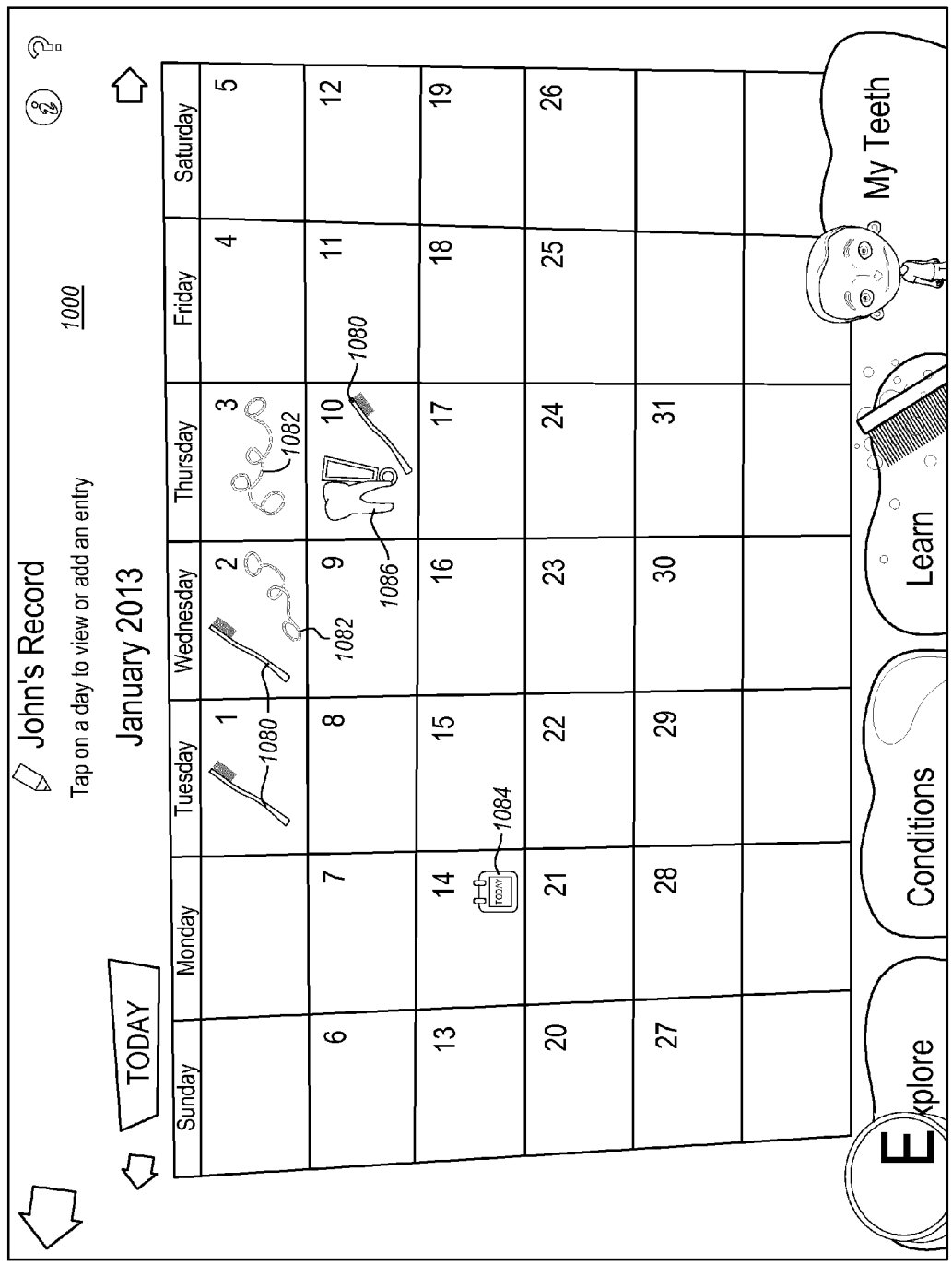
FIG. 10 illustrates an interface that includes a calendar displaying logged events.

FIG. 10 illustrates an embodiment of a calendar interface 1000 that can be used to display events that have been catalogued and saved and/or accessed by the user's computing device. This interface 1000 can be displayed in response to selecting a link, such as link 108, 208, 308, 408 or another link.

In some embodiments, the events logged with interface 900 from FIG. 9 are displayed with event icons, such as event icon 1086.

Some events correspond to behaviors, such a flossing and brushing, which can also be logged at interface 900 or another interface. In the present embodiment, days in which a user has brushed and flossed are reflected by the brushing icons 1080 and flossing icons 1082.

In other embodiments, the brushing and flossing icons 1080, 1082 are displayed to show days in which the user practiced brushing and flossing with the interfaces shown and described in reference to FIGS. 5-8.

As shown on January 2 and January 10, multiple events can be represented in a single day.

In some instances, the current date is highlighted in the calendar with a date icon 1084. The date icon 1084 can operate as a reminder and to further clarify relative timing for a user. For instance, the date icon 1084 can prompt a user to log a new event and can help the user quickly identify how long it has been since another event or behavior has been logged by visually identifying the number of days between the current date icon 1084 and any other displayed event icons.

A user can add new behavior and event icons to the calendar by entering the events in the event cataloguing interface 900 or by selecting one of the displayed days from the calendar. Selection of a day from the calendar will initiate the display of the cataloguing interface 900 or another interface for receiving information related to a behavior or event which, when entered, initiates a corresponding display of a related icon on the calendar.

The interface 1000 accesses the logged event data from the user's storage device or a third party storage and displays the corresponding event icons when the calendar is displayed.

A medical professional can access the calendar, in some embodiments, from the medical office to review and discuss the events and behaviors with the patient. In some embodiments, this tracking and review process is used to facilitate the rewarding of children for their diligent efforts in flossing and brushing by a dentist or orthodontist.

Figure 11:
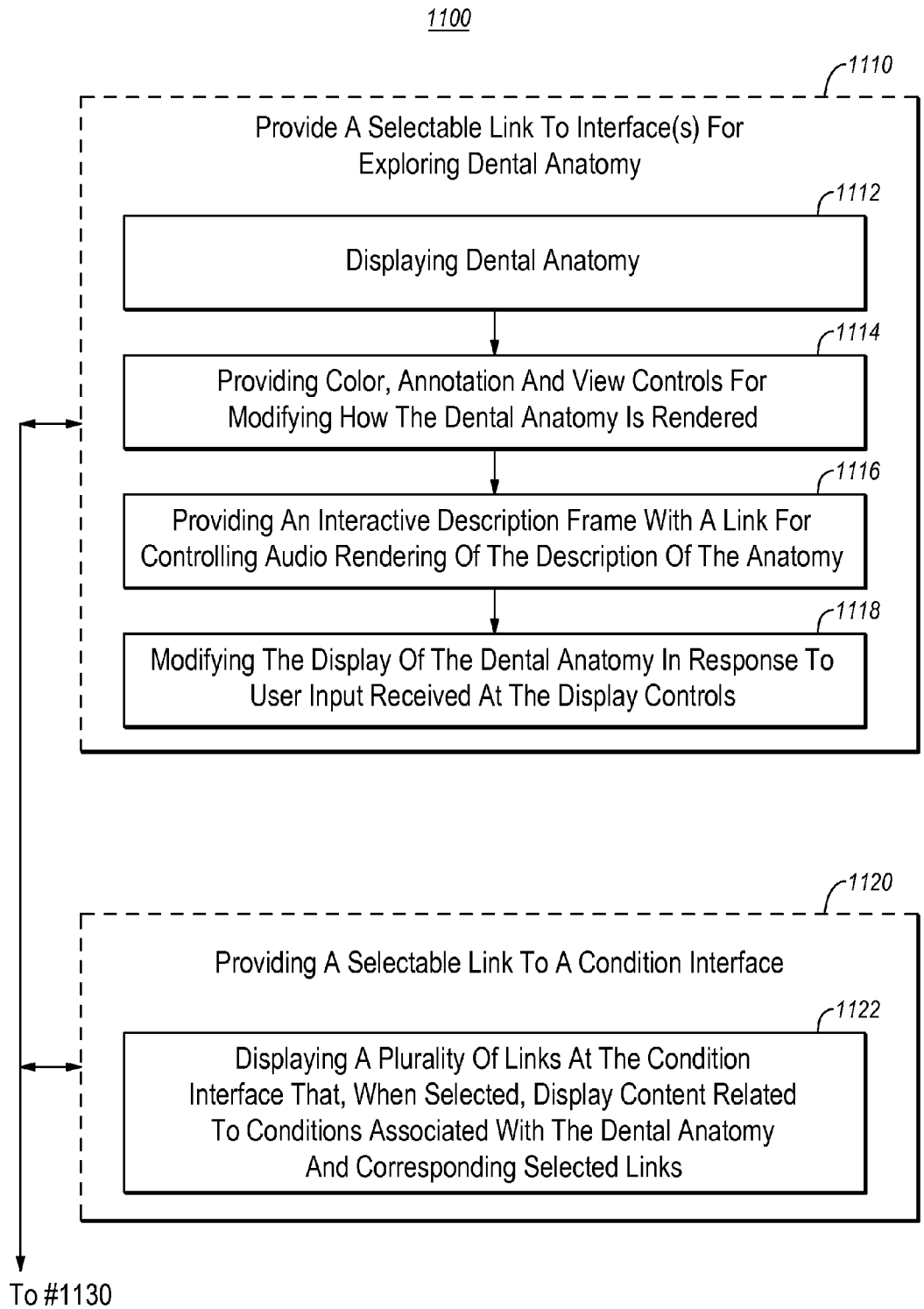
FIG. 11 illustrates a flow diagram of various acts that are associated with the methods of the invention.
Figure 11:
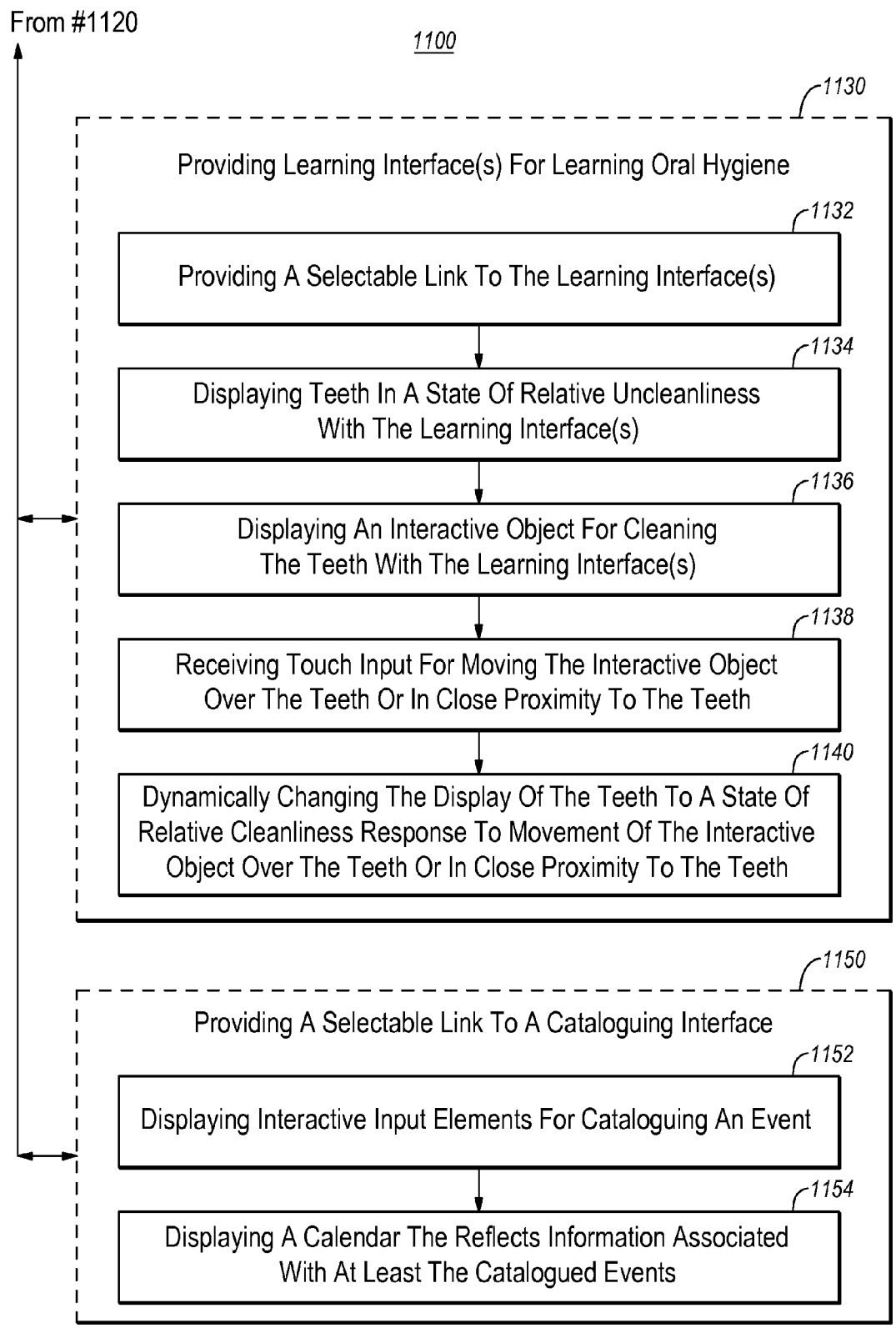

Attention will now be directed to FIG. 11, which illustrates a flow diagram of various acts that are associated with the methods of the invention.

As shown, this illustrated flow diagram includes the presentation of one or more selectable links to interfaces for exploring dental anatomy (1100). These links can include the 'explore' links described above (e.g., 102, 202, 302 and 402) or any other link. When such a link is selected, the methods of the invention include displaying dental anatomy (1112), providing color, annotation and view controls for modifying how the dental anatomy is rendered (1114) and providing an interactive description frame with a link for controlling audio rendering of the description of the anatomy (1116), and modifying the display of the dental anatomy in response to user input received at the display controls (1118), as shown and described with respect to at least FIGS. 1 and 2. Such embodiments can also include providing the information frames and corresponding information, as described.

The illustrated flow diagram 1100 also includes the presentation of a selectable link (e.g., 104, 204, 304, 404 or other link) to a condition interface (1120), such as the interface shown in FIG. 3. As described above, this interface displays a plurality of additional condition links that, when selected, display content related to conditions associated with the dental anatomy and corresponding selected links (1122). In some embodiments, this includes the presentation of multimedia content.

Methods of the invention also include providing one or more learning interfaces for learning oral hygiene (1130). These interfaces can be accessed through a corresponding learning link (e.g., 106, 206, 306, 406 or other link) (1132). When displayed, these learning interfaces display teeth in a state of relative uncleanliness (1134), displaying one or more interactive objects for cleaning the teeth (1136), receive and detect touch input for moving the interactive object(s) over the teeth or in close proximity to the teeth (1138), and dynamically change the display of the teeth to a state of relative cleanliness response to movement of the interactive object(s) over the teeth or in close proximity to the teeth (1140), as described above with reference to at least FIGS. 5-8.

Selectable links 108, 208, 308, 408 or other links are also provided to a cataloguing interface (1150) which displays interactive input elements for cataloguing an event (1152) as described in reference to FIG. 9. A corresponding calendar is also provided through one of the selectable links 108, 208, 308, 408 (when selected), which displays information associated with at least one of the catalogued events (1154) and which can include the behaviors (e.g., practice flossing and brushing) that are detected by the interfaces of the invention.

It will be appreciated that the foregoing elements of flow diagram 1100 can be performed in different orders and sequences, depending on the manner in which the users interact with the interfaces of the invention. However, it is preferable that the interfaces of the invention are all operably linked together, such that a user can navigate between the different interfaces when desired, such as, for example by selecting the various links at the bottom of the interface displays (e.g., the explore, conditions, learn and my teeth links).

In the foregoing descriptions, various interfaces have been shown and described. It will be appreciated, however, that different types of user interface menus can also be utilized alone and/or in combination with the described interfaces to facilitate the methods of the invention. Various non-limiting examples of such interface menus are shown and/or described in the following documents, which documents are all incorporated herein by reference in their entireties: U.S. patent application Ser. No. 13/093,272, filed Apr. 25, 2011; U.S. patent application Ser. No. 13/167,610, filed Jun. 23, 2011; U.S. patent application Ser. No. 13/167,600, filed Jun. 23, 2011; U.S. patent application Ser. No. 13/237,530, filed Sep. 20, 2011; U.S. patent application Ser. No. 13/477,794, filed May 22, 2012; U.S. patent application Ser. No. 13/663,820, filed Oct. 30, 2012; U.S. patent application Ser. No. 13/720, 196, filed Dec. 19, 2012; and U.S. patent application Ser. No. 13/747,595, filed Jan. 23, 2013.

Computing Environment(s)

Embodiments of the present invention may comprise or utilize special purpose or general-purpose computing devices that include computer hardware, such as, for example, one or more processors and system memory, as discussed in greater detail below. Embodiments within the scope of the present invention also include physical and other computer-readable and recordable type media for storing computer-executable instructions and/or data structures. Such computer-readable recordable media can be any available media that can be accessed by a general purpose or special purpose computer system, including volatile and non-volatile media. Computer-readable media that store computer-executable instructions according to the invention are recordable-type storage media or other physical computer storage media (devices) that are distinguished from merely transitory carrier waves or signals.

Computer-readable media that carry computer-executable instructions are transmission media. Thus, by way of example, and not limitation, embodiments of the invention can comprise at least two distinctly different kinds of computer-readable media: computer storage media (devices) and transmission media.

Computer storage media (devices) includes RAM, ROM, EEPROM, CD-ROM, DVD-ROM, HD-DVD, BLU-RAY or other optical disk storage, magnetic disk storage or other magnetic storage devices, or any other medium which can be used to store desired program code means in the form of computer-executable instructions or data structures and which can be accessed by a general purpose or special purpose computer and which are recorded on one or more recordable type medium (device). In this regard, computer storage media is distinguished from mere carrier waves, propagated signals or other transmission media.

A "network" is defined as one or more data links or communication channels that enable the transport of electronic data between computer systems and/or modules and/or other electronic devices. When information is transferred or provided over a network or another communications connection or channel (either hardwired, wireless, or a combination of hardwired or wireless) to a computer, the computer properly views the connection as a transmission medium. Transmissions media can include a network and/or data links which can be used to carry or desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (devices) or vice versa. For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that computer storage media (devices) can be included in computer system components that also (or even primarily) utilize transmission media.

Computer-executable instructions comprise, for example, instructions and data which, when executed at one or more processor, cause one or more general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described herein. Rather, the described features and acts are disclosed as example forms of implementing the claims.

Those skilled in the art will appreciate that the invention may be practiced in network computing environments with many types of computer system configurations, including personal computers, desktop computers, laptop/notebook computers, message processors, hand-held devices, multiprocessor systems, microprocessor-based or programmable consumer electronics, network PCs, minicomputers, mainframe computers, tablets, mobile telephones, PDAs, pagers, routers, switches, and the like. The invention may also be practiced in distributed and cloud system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Figure 12:
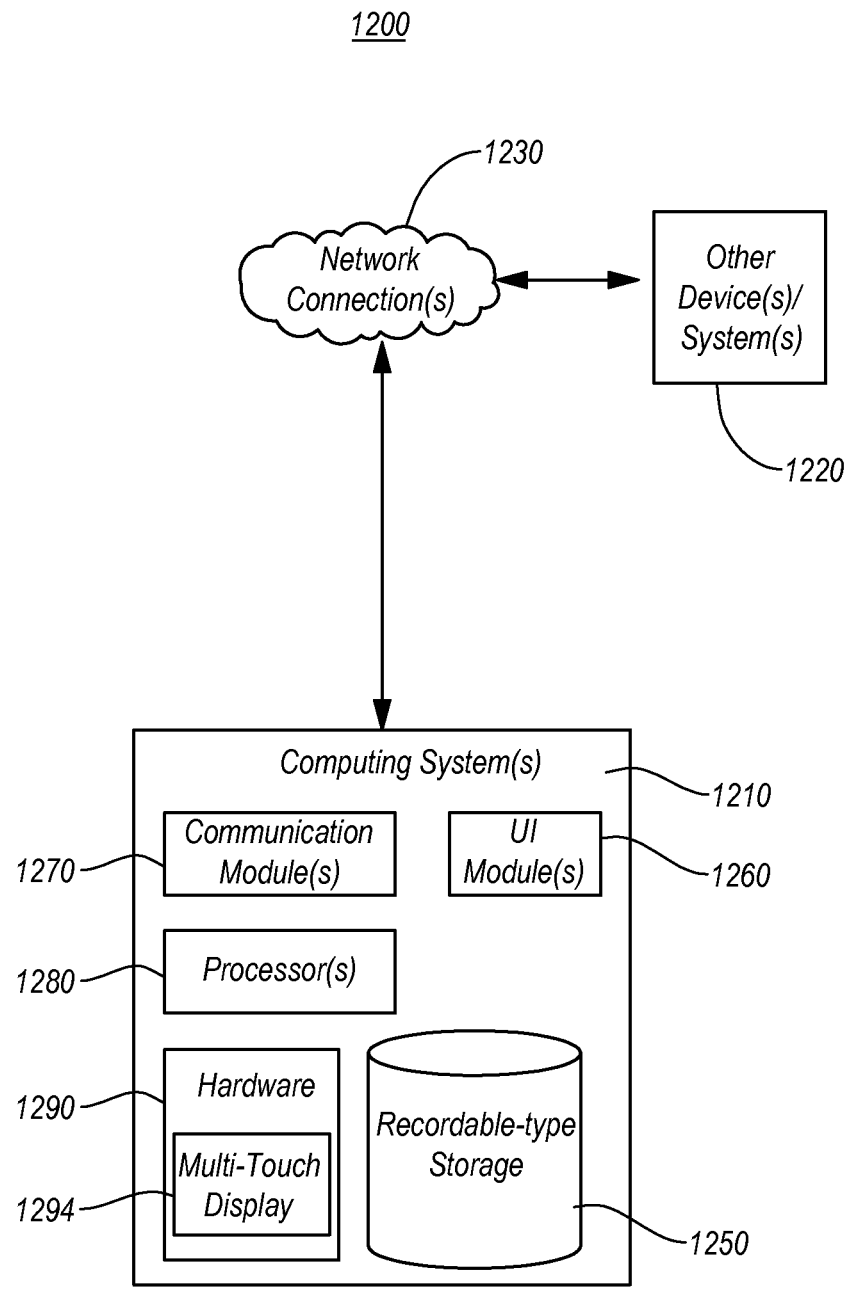
FIG. 12 illustrates one example of a computing environment that can be utilized to implement aspects of the invention.

FIG. 12 illustrates an exemplary computing environment 1200 that can be used to present the user interfaces of the invention, to facilitate user interaction with anatomical structures rendered on the user interfaces, and to demonstrably reflect the impact of various conditions and treatments on those anatomical structures.

As shown, the computing environment 1200 includes one or more computing systems 1210 in communication with one or more other devices and/or systems 1220 through one or more network connections 1230. The other systems and devices can be output and input devices, servers, proxies, or any other systems or devices. The network connections 1230 can be wired and/or wireless connections and can include any combination of Local Area Network ("LAN") connections, Wide Area Network ("WAN") connections, including the Internet and one or more proxy servers.

As illustrated, the computing system 1210 is configured with a storage 1250 that has stored computer-executable instructions for implementing the methods of the invention. The storage 1250 also stores medical record data (e.g., annotations, medical diagnosis data, condition data, image data, and so forth), and other data that is displayed with the interfaces of the invention.

The storage 1250 also store modules, such as the user interface (UI) module 1260 and the communication module 1270, which each comprise computer-executable instructions and data structures for implementing aspects of the invention.

The communication module 1270, for instance, includes computer-executable instructions that, when executed by one or more processors 1280 are operable to facilitate wireless and/or wired communications through the network connections 1230 to access or transmit data associated with the interfaces described herein, including the interfaces themselves, to medical professionals and other computing systems. The communication modules are also configured to encrypt and decrypt data and to perform authentication of user and system credentials.

The interface module 1260 includes computer-executable instructions that, when executed by the one or more processors 1280 are operable to generate and/or present the user interfaces described above. Interface module 1260 also provides computer-executable instructions that, when executed, are operable to detect and process user input and to perform the functionality described above, such as, but not limited brushing teeth and flossing with the interactive toothbrush and interactive floss shown in FIGS. 5-8.

The data stored at storage 1250 can also include any of the interfaces and data described in reference to the following patent applications, each of which is incorporated herein by reference its entirety, and such that the present invention can incorporate any combination of functionality described in this document as well as any of the functionality described in the following documents: U.S. patent application Ser. No. 13/093,272, filed Apr. 25, 2011; U.S. patent application Ser. No. 13/167,610, filed Jun. 23, 2011; U.S. patent application Ser. No. 13/167,600, filed Jun. 23, 2011; U.S. patent application Ser. No. 13/237,530, filed Sep. 20, 2011; U.S. patent application Ser. No. 13/477,794, filed May 22, 2012; U.S. patent application Ser. No. 13/663,820, filed Oct. 30, 2012; U.S. patent application Ser. No. 13/720,196, filed Dec. 19, 2012; and U.S. patent application Ser. No. 13/747,595, filed Jan. 23, 2013.

The storage 1250 can comprise, but is not limited to, non-volatile disk storage and volatile memory. It will also be appreciated that the storage 1250 can be distributed among a plurality of different devices or systems, including the other illustrated system(s)/device(s) 1220, and does not necessarily need to be constrained to a single physical device. In some embodiments, however, the storage 1250 is limited to local storage of the computing system 1210.

In some embodiments, the computing system 1210 comprises a wireless cell phone, a tablet computer, a notebook computer, a PDA, and/or any other type of smart device having a display screen 1294, speakers and other hardware 1290 for rendering image data, audio data, and/or textual data to a user via the interfaces (1260, 1270) of the system (1210), for example. In some embodiments, the hardware 1290 of the system 1210 includes a display screen 1294 that is a multi-touch screen capable of receiving touch input.

The computing systems of the invention can include mobile devices (e.g., phones, tablets, notebook computers, portable gaming device, etc.) and stationary device (e.g., desktop computers, gaming consoles, televisions, servers, kiosks, etc.).

It will be appreciated that the system hardware 1290 can include any output device (e.g., display screen, speakers, printer, etc.), as well as any input device (keyboard, mouse, microphone, touchpad, etc.).

Each of the other connected systems/devices 1220 also includes hardware, processor and storage components similar to those described above with respect to system 1210.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

I claim:

1. A hardware storage device having stored computer-executable instructions which, when executed by at least one computing processor, implement a method for presenting and using a computer interface for oral hygiene, wherein the method includes:
   displaying an interface with a first link that is operable, when selected, to access an interactive tooth brushing interface, the interactive tooth brushing interface comprising:
      a display of at least one tooth at a display screen of a computing system; and
      an interactive toothbrush, the interactive toothbrush being operable to be moved over the at least one tooth in response to user touching and dragging the toothbrush with touch input entered at the display screen,
      wherein the display of the at least one tooth changes from a first display state to a second display state that is relatively cleaner than the first display state in response to the toothbrush being selectably moved over the tooth,
   displaying the interface with a second link that is operable, when selected, to access an interactive flossing interface, the interactive flossing interface comprising:
      one or more object in close proximity to the at least two teeth; and
      interactive floss that is operable to be selectably moved over the at least two teeth and one or more object in response to separate touch inputs that are simultaneously received at the display screen, the simultaneous touch inputs being received at different locations relative to the at least two teeth,
      wherein the interactive floss is dynamically moved in response to movement of the separate touch inputs such that the interactive floss is persistently displayed between the separate touch inputs even when the locations of the separate touch inputs are moved; and
      wherein the one or more object is removed from close proximity to the at least two teeth when the interactive floss is moved over the one or more object in close proximity to the at least two teeth, dynamically in response to detected movement of the separate touch inputs.

2. The storage device of claim 1, wherein the method further includes:
   detecting a relative distance between the separate touch inputs and determining that the relative distance between the separate touch inputs remains within a predetermined threshold of variability during the movement of the floss.

3. The storage device of claim 1, wherein the method further includes:
dynamically changing a display state of a plurality of teeth simultaneously in response to the toothbrush being selectably moved over the plurality of teeth.

4. The storage device of claim 1, wherein the method further includes:
gradually changing the display state from the first display state to the second display state.

5. The storage device of claim 1, wherein the method further includes:
abruptly changing the display state from the first display state to the second display state.

6. The storage device of claim 1, wherein the method further includes:
rendering an audible brushing sound when the interactive brush is moved over the teeth.

7. The storage device of claim 1, wherein the method further includes:
displaying the interface with a first and second links in response to a user selection of a learning link on a primary interface display.

8. The storage device of claim 7, wherein the method further includes:
displaying the primary interface display with the learning link and a condition link, the condition link being operable, when selected, to display links to a plurality of dental conditions, the links to the plurality of dental conditions being operable, when selected, to render multimedia content related to the dental conditions.

9. The storage device of claim 7, wherein the method further includes:
displaying the primary interface display with the learning link and a link to an interactive display of an anatomical object.

10. The storage device of claim 9, wherein the method further includes:
displaying the anatomical object at the interactive display in response to receiving user input selecting the link to the interactive display; and
displaying a plurality of display controls that include at least an annotation control, a view control and a color control.

11. The storage device of claim 10, wherein the method further includes:
displaying an information frame with the plurality of display controls, the information frame with a handle that is selectable to display and hide the information frame.

12. The storage device of claim 10, wherein the method further includes:
displaying the anatomical object with a plurality of teeth, wherein different teeth are colored differently in response to a setting of the color control.

13. The storage device of claim 7, wherein the method further includes:
displaying the primary interface display with the learning link and an event link, the event link being operable, when selected, to display a calendar with icons corresponding to a plurality of events associated with dental hygiene.

14. The storage device of claim 13, wherein the method further includes:
adding a new icon to the calendar in response to a user selecting a day from the calendar and adding event data to event fields that are displayed in response to the selection of the day from the calendar.

15. The storage device of claim 1, wherein the method further includes:
displaying a perception scale with the event fields, the perception scale including a plurality of selectable icons associated with a perceived feelings related to the event data.

16. The storage device recited in claim 1, wherein the computing system is a mobile computing system.

17. A computer implemented method for presenting and using a computer interface for oral hygiene, wherein the method includes:
displaying an interface with a first link that is operable, when selected, to access an interactive flossing interface, the interactive flossing interface comprising:
a display of at least two teeth at a display screen of a computing device;
one or more object in close proximity to the at least two teeth; and
interactive floss that is operable to be selectably moved over the at least two teeth and one or more object in response to separate touch inputs that are simultaneously received at the display screen, the simultaneous touch inputs being received at different locations relative to the at least two teeth,
wherein the interactive floss is dynamically moved in response to movement of the separate touch inputs, such that the interactive floss is persistently displayed between the separate touch inputs even when the locations of the separate touch inputs are moved, and
wherein the one or more object is removed from close proximity to the at least two teeth when the interactive floss is moved over the one or more object in close proximity to the at least two teeth, dynamically in response to detected movement of the separate touch inputs; and
displaying the interface with a second link that is operable, when selected, to access an interactive flossing interface, the interactive tooth brushing interface comprising:
a display of at least one tooth at the display screen; and
an interactive toothbrush being operable to be moved over the at least one tooth in response to user touching and dragging the toothbrush with touch input entered at the display screen,
wherein the display of the at least one tooth dynamically changes from a first display state to a second display state that is relatively cleaner that the first display state in response to the toothbrush being selectably moved over the tooth.

18. A computing device comprising:
at least one hardware processor;
a display screen; and
one or more hardware storage media having stored computer-executable instructions which, when executed by the at least one hardware processor, implement a method for presenting and using a computer interface for oral hygiene, wherein the method includes:
displaying a particular one tooth with a first display state of relative uncleanliness at the display screen; and
displaying an interactive toothbrush, the interactive toothbrush being operable to be moved over the particular tooth in response to user touching and dragging the toothbrush with touch input entered at the display screen, wherein the display of the particular tooth dynamically changes from the first display state to a second display state of relative cleanliness in response to the toothbrush being selectably moved over the particular tooth; and displaying at least two teeth at the display screen with one or more object in close proximity to the at least two teeth; and displaying interactive floss that is operable to be selectably moved over the one or more object in proximity to the at least two teeth in response to separate touch inputs that are simultaneously received and detected at the display screen, the simultaneous touch inputs being received at different locations relative to the at least two teeth; and moving the interactive floss dynamically in response to movement of the separate touch inputs, such that the interactive floss is persistently displayed between the separate touch inputs even when the locations of the separate touch inputs are moved, and wherein the one or more object is removed from close proximity to the at least two teeth when the interactive floss is moved over the one or more object in close proximity to the at least two teeth in response to detected movement of the separate touch inputs.

\* \* \* \* \*